(12) United States Patent
Wang et al.

(10) Patent No.: US 11,007,510 B2
(45) Date of Patent: May 18, 2021

(54) SUPPORTED ε/ε' IRON CARBIDE CATALYST FOR FISCHER-TROPSCH SYNTHESIS REACTION, PREPARATION METHOD THEREOF AND FISCHER-TROPSCH SYNTHESIS PROCESS

(71) Applicants: China Energy Investment Corporation Limited, Beijing (CN); National Institute of Clean-and-Low-Carbon Energy, Beijing (CN)

(72) Inventors: Peng Wang, Beijing (CN); Kui Zhagn, Beijing (CN); Yijun Lv, Beijing (CN); Quan Lin, Beijing (CN); Bo Feng, Beijing (CN); Zhuowu Men, Beijing (CN); Fengbo Zhang, Beijing (CN); Qi Sun, Beijing (CN); Ping Miao, Beijing (CN)

(73) Assignees: CHINA ENERGY INVESTMENT CORPORATION LIMITED, Beijing (CN); NATIONAL INSTITUTE OF CLEAN-AND-LOW-CARBON ENERGY, Beijing (CN)

( * ) Notice: Subject to any disclaimer, the term of this patent is extended or adjusted under 35 U.S.C. 154(b) by 0 days.

(21) Appl. No.: 17/044,694

(22) PCT Filed: Jun. 21, 2018

(86) PCT No.: PCT/CN2018/092084
§ 371 (c)(1),
(2) Date: Oct. 1, 2020

(87) PCT Pub. No.: WO2019/192079
PCT Pub. Date: Oct. 10, 2019

(65) Prior Publication Data
US 2021/0031174 A1    Feb. 4, 2021

(30) Foreign Application Priority Data
Apr. 2, 2018    (CN) .......................... 201810283256.6

(51) Int. Cl.
*B01J 27/22*    (2006.01)
*B01J 21/08*    (2006.01)
(Continued)

(52) U.S. Cl.
CPC .............. *B01J 27/22* (2013.01); *B01J 21/04* (2013.01); *B01J 21/063* (2013.01); *B01J 21/08* (2013.01); *B01J 35/026* (2013.01); *B01J 37/0221* (2013.01); *B01J 37/0236* (2013.01); *B01J 37/088* (2013.01); *B01J 37/18* (2013.01); *C07C 1/044* (2013.01); *C10G 2/32* (2013.01); *C07C 2521/04* (2013.01); *C07C 2521/06* (2013.01); *C07C 2521/08* (2013.01); *C07C 2523/745* (2013.01)

(58) Field of Classification Search
CPC ... C10G 2/32; C07C 2521/06; C07C 2521/08; C07C 2521/04; C07C 2523/745; B01J 27/22; B01J 21/08; B01J 21/04; B01J 21/063; B01J 35/026; B01J 37/0221; B01J 37/088; B01J 37/18
See application file for complete search history.

(56) References Cited

U.S. PATENT DOCUMENTS

| 9,776,175 B2 | 10/2017 | Chun et al. |
| 2004/0009871 A1 | 1/2004 | Hu et al. |

(Continued)

FOREIGN PATENT DOCUMENTS

| CN | 104399501 | 3/2015 |
| CN | 105195189 | 12/2015 |

(Continued)

OTHER PUBLICATIONS

PCT International Search Report and Written Opinion (with English translation) for corresponding PCT Application No. PCT/CN2018/092084, dated Jan. 4, 2019, 9 pages.

(Continued)

*Primary Examiner* — Jafar F Parsa
(74) *Attorney, Agent, or Firm* — Dority & Manning, P.A.

(57) ABSTRACT

The present disclosure relates to the technical field of Fischer-Tropsch synthesis reaction catalysts, and discloses a supported ε/ε' iron carbide catalyst for Fischer-Tropsch synthesis reaction, preparation method thereof and Fischer-Tropsch synthesis process, wherein the method comprises the following steps: (1) dipping a catalyst carrier in a ferric salt aqueous solution, drying and roasting the dipped carrier to obtain a catalyst precursor; (2) subjecting the catalyst precursor and $H_2$ to a precursor reduction at the temperature of 300-550° C.; (3) pretreating the material obtained in the step (2) with $H_2$ and CO at the temperature of 90-185° C., wherein the molar ratio of $H_2/CO$ is 1.2-2.8:1; (4) preparing carbide with the material obtained in the step (3), $H_2$ and CO at the temperature of 200-300° C., wherein the molar ratio of $H_2/CO$ is 1.0-3.2:1. The preparation method has the advantages of simple and easily obtained raw materials, simple and convenient operation steps, being capable of preparing the catalyst with 100% pure phase ε/ε' iron carbide as the active phase, the catalyst has lower selectivity of $CO_2$ and $CH_4$ and higher selectivity of effective products.

18 Claims, 4 Drawing Sheets

(51) Int. Cl.
- *B01J 21/04* (2006.01)
- *B01J 21/06* (2006.01)
- *B01J 35/02* (2006.01)
- *B01J 37/02* (2006.01)
- *B01J 37/08* (2006.01)
- *B01J 37/18* (2006.01)
- *C07C 1/04* (2006.01)
- *C10G 2/00* (2006.01)

(56) References Cited

U.S. PATENT DOCUMENTS

| | | |
|---|---|---|
| 2012/0245236 A1 | 9/2012 | Suib et al. |
| 2014/0360917 A1 | 12/2014 | Park et al. |
| 2016/0096167 A1 | 4/2016 | Park et al. |

FOREIGN PATENT DOCUMENTS

| | | |
|---|---|---|
| CN | 10578020 A | 7/2016 |
| CN | 105728020 | 7/2016 |

OTHER PUBLICATIONS

Santos et al. "Metal organic framework-mediated synthesis of highly active and stable Fischer-Tropsch catalysts," *Nature Communications*, Mar. 5, 2015—8 pages.

Smit et al, "Stability and reactivity of ε-χ-θ iron carbide catalyst phases in Fischer—Tropsch synthesis: Controlling μC," *Journal of the American Chemical Society (JACS)*, Vo. 132, No. 42, Oct. 6, 2010, pp. 14928-14941.

Kahyarian et al., "CO2 corrosion of mild steel,"Trends in Oil and Gas Corrosion Research and Technologies, 2017—42 pages.

National Energy Technology Laboratory, "10.2 Fischer-Tropsch Synthesis,"https://www.netl.doe.gov/research/coal/energy-systems/gasifipedia/ftsynthesis, Retrieved on Feb. 17, 2021—4 pages.

Xu et al., "ε-Iron carbide as a low-temperature Fischer-Tropsch synthesis catalyst"*Nature Communications*, Dec. 12, 2014, Nature Communications, Article No. 5783, DOI:10.108/ncomms6783—8 pages.

Accompanying Drawings

SUPPORTED ε/ε' IRON CARBIDE CATALYST FOR FISCHER-TROPSCH SYNTHESIS REACTION, PREPARATION METHOD THEREOF AND FISCHER-TROPSCH SYNTHESIS PROCESS

FIELD

The present disclosure relates to the technical field of Fischer-Tropsch synthesis reaction catalysts, in particular to a supported ε/ε' iron carbide catalyst for Fischer-Tropsch synthesis reaction, a preparation method thereof and a Fischer-Tropsch synthesis process.

BACKGROUND

The structure of primal)/energy in the People's Republic of China (PRC) is characterized by rich coal and insufficient oil and gas, the degree of dependence on the imported petroleum in China has continuously rising along with the rapid economic development, which reaches 61% in 2015, thereby severely impact the energy safety in China. Fischer-Tropsch synthesis can convert synthesis gas consisting of carbon monoxide and hydrogen into liquid fuels and chemicals, it has emerged as an increasingly important energy conversion pathway in recent years. The indirect coal liquefaction technology based on Fischer-Tropsch synthesis may be used for realizing clean utilization of coal and partially alleviating the problem that the China heavily depends on the imported petroleum, the technology has become one of the preferred technologies for replacing petroleum with coal and clean utilization of coal in China. Due to the industrial efforts for years, the iron-based coal indirect liquefaction technical industrial demonstration project with a production capacity of 160,000 tons/year has put into operation in China; in addition, the iron-based coal indirect liquefaction plants with a production capacity of 1 million tons/year invested by Shandong Yankuang Group and other companies and the iron-based coal indirect liquefaction plants with a production capacity of 4 million tons/year invested by Shenhua Ningxia Coal Industry Group Co., Ltd. have put into pilot run.

The reaction formulas for the Fischer-Tropsch synthesis are as follows:

$$(2n+1)H_2 + nCO \rightarrow C_nH_{2n+2} + nH_2O \quad (1)$$

$$2nH_2 + nCO \rightarrow C_nH_{2n} + nH_2O \quad (2)$$

Besides the final products alkanes and alkenes, the industrial Fischer-Tropsch synthesis can also produce the byproducts carbon dioxide ($CO_2$) and methane ($CH_4$). The Fischer-Tropsch synthesis reaction has a complex mechanism and numerous steps, such as CO dissociation, carbon (C) hydrogenation, $CH_x$ chain growth, and the hydrogenation and dehydrogenation reactions which result in the desorption of hydrocarbon products and the removal of oxygen (O). From the viewpoint of practical application, the main purpose of improving the Fischer-Tropsch synthesis catalyst is to increase selectivity of the target products, reduce selectivity of the byproducts, enhance stability of the catalyst and prolong service life of the catalyst.

Iron is the cheapest transition metal used in the manufacture of Fischer-Tropsch synthesis catalysts. The active phase of iron-based Fischer-Tropsch catalysts is generally considered to be iron carbide. The traditional iron-based catalyst has high activity of water gas conversion ($CO+H_2O \rightarrow CO_2 + H_2$), so the traditional iron-based catalyst usually has high selectivity of a byproduct $CO_2$, which generally accounts for 25%-45% of the conversion raw material carbon monoxide. This is one of the major disadvantages of iron-based catalysts for the Fischer-Tropsch synthesis reaction.

It is difficult to synthesize the pure phase of iron carbide, which is the active phase of the iron-based Fischer-Tropsch synthesis catalyst. The active phase of the iron-based catalyst has very complicated variation, it causes considerable debates on the nature of the active phase and the Fischer-Tropsch synthesis reaction mechanism of the iron-based catalyst. The different carbides have been observed under the Fischer-Tropsch reaction conditions, including ε-$Fe_2C$, ε-$Fe_{2.2}C$, $Fe_7C_3$, χ-$Fe_5C_2$ and θ-$Fe_3C$. The article "Stability and reactivity of ε-χ-θ iron carbide catalyst phases in Fischer-Tropsch synthesis: Controlling $\mu_C$" published on the top-level *Journal of the American Chemical Society (JACS) in* 2010 provides a systematic calculation and experiment of the conditions for generating the various iron carbides, as shown FIG. 1, the occurrence of phase transition of iron carbides (ε-χ-θ phase transition) depends on the temperature and the $H_2$/CO ratio. Specifically, high temperature low carbon chemical potential ($\mu_C$), i.e., high $H_2$/CO ratio, generally results in preferential formation of iron carbide θ-$Fe_3C$; conversely, the high $\mu_C$ (low $H_2$/CO ratio) and moderate temperature (~250° C.) are conducive to formation of iron carbide χ-$Fe_5C_2$; the ε-carbide is preferentially formed at lower temperatures, and higher carbon chemical potential $\mu_C$.

Figure 1:
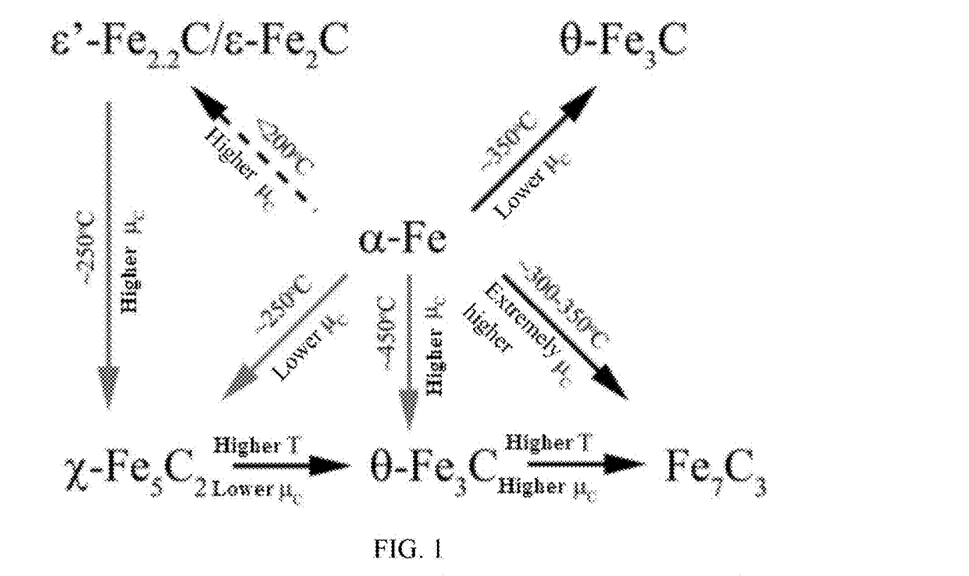
FIG. 1 shows a conversion relationship graph of the iron carbides in the prior art.

Its main viewpoint is as shown in FIG. 1, the article adopts $Fe_2O_3$ as an initiative precursor, a series of experiments are carried out in the Fischer-Tropsch synthesis reaction atmosphere, and the phase change of the product is tested by the X-ray Diffraction (XRD) and the synchrotron radiation in-situ X-ray Absorption Fine Structure Spectroscopy (XAS). At a higher carbon chemical potential $\mu_C$, the ε/ε' iron carbide needs to be generated and stably existed at a mild condition of ~200° C., and when the temperature is close to 250° C., the ε/ε' iron carbide is converted into χ-$Fe_5C_2$ which has a thermodynamic stability. In the industrial Fischer-Tropsch synthesis production, the iron-based Fischer-Tropsch synthesis temperature is within a range of 235-265° C., in order to increase the saturated vapor pressure of the byproduct steam, obtain high-quality steam and improve the economic benefit. In other words, the authoritative article indicates that the ε/ε' iron carbide is unstable at a temperature above 200° C., thus cannot be used as a catalyst suitable for the modern Fischer-Tropsch synthesis industry.

The article "Metal organic framework-mediated synthesis of highly active and stable Fischer-Tropsch catalysts" published in 2015 on *Nature communication*, a subsidiary of the top-level Journal *Nature*, provides an attempt of synthesizing the carbides, and successfully synthesizes χ-$Fe_5C_2$, which is a catalyst that can be used at the industrial temperatures of modern Fischer-Tropsch synthesis, however; its $CO_2$ selectivity is as high as 46%, which means that its theoretically maximum CO utilization efficiency is only 54%, the production efficiency is relatively low.

CN104399501A discloses a method for preparing ε-$Fe_2C$ nanoparticles suitable for low-temperature Fischer-Tropsch synthesis reaction. The initial precursor is a skeleton iron material, and the reaction system is intermittent discontinuous reaction of polyethylene glycol solvent. The catalyst has a $CO_2$ selectivity of 18.9% and a $CH_4$ selectivity of 17.3%. Its disadvantages are that the preparation method can only be applied at a low temperature less than 200° C., and the reaction cannot be continuously performed. It means that the catalyst is not suitable for continuous production under modern Fischer-Tropsch synthesis industrial conditions.

Among the aforementioned technologies, each has the problems such as complicated preparation process, expensive raw materials, poor catalyst stability, and excessively high selectivity of by-product $CO_2$ or $CH_4$.

SUMMARY

The present disclosure aims to overcome the technical problems in the prior art and provides a supported ε/ε' iron carbide catalyst for Fischer-Tropsch synthesis reaction, a preparation method thereof and a Fischer-Tropsch synthesis process.

In order to fulfill the above purpose, a first aspect of the present disclosure provides a method of preparing a supported ε/ε' iron carbide catalyst for Fischer-Tropsch synthesis reaction, wherein the preparation method comprises the following steps:

(1) dipping a catalyst carrier in a ferric salt aqueous solution, drying and roasting the dipped carrier to obtain a catalyst precursor;

(2) subjecting the catalyst precursor and $H_2$ to a precursor reduction at the temperature of 300-550"C;

(3) pretreating the material obtained in the step (2) with $H_2$ and CO at the temperature of 90-185° C., wherein the molar ratio of $H_2$/CO is 1.2-2.8:1;

(4) preparing carbide with the material obtained in the step (3), $H_2$ and CO at the temperature of 200-300° C., wherein the molar ratio of $H_2$/CO is 1.0-3.2:1.

In a second aspect, the present disclosure provides a supported ε/ε' iron carbide catalyst for Fischer-Tropsch synthesis reaction obtained with the preparation method of the present disclosure.

In a third aspect, the present disclosure provides a Fischer-Tropsch synthesis process comprising: contacting a synthesis feed gas with a catalyst under the Fischer-Tropsch synthesis reaction conditions, wherein the catalyst is the supported ε/ε' iron carbide catalyst for the Fischer-Tropsch synthesis reaction of the present disclosure.

The present disclosure has the following technical effects:

(1) The required raw materials are simple and easily obtained, and the cost is low. The iron source applied as the main raw material for synthesizing the precursor can be commercially available ferric salt, when the active phase carbide is synthesized, only the original reaction gas (carbon monoxide and hydrogen) of a Fischer-Tropsch synthesis reaction system is utilized, it does not involve with any inorganic or organic reaction raw material, such that the raw materials are greatly simplified compared with the prior art recited in the literatures;

(2) The preparation method has simple and convenient operation steps, and in the preferred embodiment, the preparation of the carbide catalyst and the Fischer-Tropsch synthesis can share the same reactor, so that an additional active phase carbide preparation reaction device is not required, the whole preparation process only needs three steps, namely precursor reduction, pretreatment and carbide preparation, the preparation and synthesis reaction of the active phase can be performed in situ in the same reactor;

(3) The method of the present disclosure can be used for preparing the active phase ε/ε' iron carbide with 100% purity supported on the carrier, the prepared supported ε/ε' iron carbide catalyst is suitable for a high-temperature and high-pressure (e.g., the temperature of 235-250° C. and the pressure of 2.3-2.5 MPa) continuous reactor, the reaction stability is extremely high, such that the theoretical technical barrier in the traditional literature theory is broken through, namely "the ε/ε' iron carbide needs to be stably existed at a mild condition of less than 200° C. at a higher carbon chemical potential $\mu_C$", the stable temperature can be up to 250° C., and the selectivity of $CO_2$ is extremely low; under the reaction conditions of industrial Fischer-Tropsch synthesis, a high-pressure continuous reactor can be used for keeping continuous and stable reaction for more than 400 hours, and the selectivity of $CO_2$ is less than 5% preferably, less than 2.5%); in addition, the selectivity of the by-product $CH_4$ is kept at 13.5% (preferably, below 9.5%), the selectivity of the effective product reaches 82% or more (preferably, 88% or more), and the preparation method is very suitable for the industrial and efficient production of oil wax products with the Fischer-Tropsch synthesis in modern coal chemical industry.

DETAILED DESCRIPTION

The terminals and any value of the ranges disclosed herein are not limited to the precise ranges or values, such ranges or values shall be comprehended as comprising the values adjacent to the ranges or values. As for numerical ranges, the endpoint values of the various ranges, the endpoint values and the individual point value of the various ranges, and the individual point values may be combined with one another to produce one or more new numerical ranges, which should be deemed have been specifically disclosed herein.

A first aspect of the present disclosure provides a method of preparing a supported ε/ε' iron carbide catalyst for Fischer-Tropsch synthesis reaction, wherein the preparation method comprises the following steps:

(1) dipping a catalyst carrier in a ferric salt aqueous solution, drying and roasting the dipped carrier to obtain a catalyst precursor;

(2) subjecting the catalyst precursor and $H_2$ to a precursor reduction at the temperature of 300-550° C.;

(3) pretreating the material obtained in the step (2) with $H_2$ and CO at the temperature of 90-185"C, wherein the molar ratio of $H_2$/CO is 1.2-2.8:1;

(4) preparing carbide with the material obtained in the step (3), $H_2$ and CO at the temperature of 200-300° C., wherein the molar ratio of $H_2$/CO is 1.0-3.2:1.

In the present disclosure, the ferric salt may be a water-soluble ferric salt commonly used in the art, and may be a commercially available product, for example, the ferric salt is at least one selected from the group consisting of iron nitrate, iron chloride and ferrous ammonium sulfate.

In the present disclosure, the catalyst carrier may be a conventional choice in the art, for example, the catalyst carrier is at least one selected from the group consisting of silica, alumina and titania. In the present disclosure, it is preferable that the catalyst carrier has a particle size within a range of 30-200 μm.

In the present disclosure, it is preferable that the dipping is performed such that the iron content in the dipped carrier after drying is within a range of 10-30 wt %. The dipping may be a conventional choice in the art as long as the supported amount of iron in the dipped carrier is achieved, and preferably, the dipping is a saturation dipping method.

According to a preferred embodiment of the present disclosure, the drying and roasting process comprises: firstly drying the dipped carrier at 20-30° C. for 0.5-4 h, then stoving the dipped carrier at 35-80° C. and the vacuum degree of 250-1,200 Pa for 6-10 h, drying the stoned material at 110-150° C. for 3-24 h, and then roasting the Obtained material at 300-550° C. for 1-10 h. The drying process may be performed in an oven, and the roasting process may be performed in a muffle furnace.

In the present disclosure, the step (2) can simultaneously play the roles of generating the nanometer iron powder in situ from the iron atoms in the precursor and carrying out surface purification treatment on the generated nanometer iron powder.

In the present disclosure, the $H_2$ in step (2) may pass through the reaction system in the form of a flow of $H_2$, the pressure of the precursor reduction treatment is controlled by controlling the pressure of the flow of $H_2$; it is preferable that in step (2), the pressure of the precursor reduction treatment is within a range of 0.1-15 atmospheric pressure, preferably 0.3-2.6 atmospheric pressure; the time is within a range of 0.7-15 h, preferably 1-12 h.

In the present disclosure, the amount of $H_2$ may be selected according to the amount of the raw material to be treated, and preferably, the gas velocity of $H_2$ in the step (2) is within a range of 600-25,000 mL/h/g, and more preferably 2,800-22,000 mL/h/g.

In the present disclosure, the $H_2$ and CO in the step (3) may pass through the reaction system in the form of ($H_2$+CO) mixed gas flow, and at the same time, the pressure of the pretreatment process is controlled by controlling the pressure of the ($H_2$+CO) mixed gas flow; it is preferable that in the step (3), the pressure of the pretreatment process is within a range of 0.05-7 atmospheric pressure, preferably 0.08-4.5 atmospheric pressure; the time is within a range of 15-120 min, preferably 20-90 min.

In the present disclosure, the total gas velocity of $H_2$ and CO in the step (3) is preferably within a range of 300-12,000 mL/h/g, and more preferably 1,500-9,000 mL/h/g.

In the present disclosure, the $H_2$ and CO in the step (4) may pass through the reaction system in the form of ($H_2$+CO) mixed gas flow, and the pressure of the carbide preparation process is controlled by controlling the pressure of the ($H_2$+CO) mixed gas flow, preferably, the pressure of the carbide preparation in step (4) is within a range of 0.1-10 atmospheric pressure, preferably 0.2-4.5 atmospheric pressure; the time is within a range of 1.5-15 h, preferably 2.5-12 h.

In the present disclosure, it is preferable that the total gas velocity of $H_2$ and CO in the step (4) is within a range of 500-30,000 mL/h/g, and more preferably 3,000-25,000 mL/h/g.

According to another preferred embodiment of the present disclosure, the preparation method further comprises: the system temperature after the pretreatment is increased to 200-300° C. at the heating rate of 0.2-5° C./min. In the preferred embodiment, the prepared phase-pure ε/ε' iron carbide catalyst may have a better selectivity of effective product in the Fischer-Tropsch synthesis reaction. Further preferably, the system temperature after the pretreatment is increased to 210-290° C. at a heating rate of 0.2-2.5/min.

Unless otherwise specified in the present disclosure, the term "mL/h/g" refers to a volume of feed gas per gram of raw material per hour.

According to another preferred embodiment of the present disclosure, the precursor reduction, pretreatment and carbide preparation process is carried out in a Fischer-Tropsch synthesis reactor. In the preferred embodiment, the catalyst preparation and the Fischer-Tropsch synthesis share the same reactor, such that the $H_2$ and CO raw materials in the catalyst preparation process may be the original raw materials of the Fischer-Tropsch synthesis reaction system, an additional active phase carbide preparation reaction device is not required; the whole preparation process may, allow that the preparation and synthesis reaction of the active phase can be performed in situ in the same reactor, and the operation steps are more simple and convenient.

In a second aspect, the present disclosure provides a supported ε/ε' iron carbide catalyst for Fischer-Tropsch synthesis reaction obtained with the preparation method of the present disclosure. The active phase of the supported ε/ε' iron carbide catalyst has 100% pure-phase ε/ε' iron carbide.

In a third aspect, the present disclosure provides a Fischer-Tropsch synthesis process comprising: contacting a synthesis feed gas with a catalyst under the Fischer-Tropsch synthesis reaction conditions, wherein the catalyst is the supported ε/ε' iron carbide catalyst for the Fischer-Tropsch synthesis reaction of the present disclosure.

The supported ε/ε' iron carbide catalyst is used as a catalyst for Fischer-Tropsch synthesis, the catalyst can perform Fischer-Tropsch synthesis reaction under high temperature and high pressure, wherein the Fischer-Tropsch synthesis reaction conditions comprise: the temperature is within a range of 235-250° C., and the pressure is within a range of 2.3-2.5 MPa.

Unless otherwise specified in the present disclosure, the pressure refers to an absolute pressure.

In the present disclosure, it is preferable that the Fischer-Tropsch synthesis is carried out in a high temperature and high pressure continuous reactor. The supported ε/ε' iron carbide catalyst of the present disclosure may allow that the Fischer-Tropsch synthesis reaction is continuously and stably performed for more than 400 hours in a high-temperature high-pressure continuous reactor.

The present disclosure will be described in detail below with reference to examples. In the following examples, CO conversion rate %=[(mole number of CO in the feedstock−mole number of CO in the discharged material)/mole number of CO in the feedstock]×100%;

$CO_2$ selectivity %=[mole number of $CO_2$ in the discharged material/(mole number of CO in the feedstock mole number of CO in the discharged material)]×100%;

$CH_4$ selectivity %=[mole number of $CH_4$ in the discharged material/(mole number of CO in the feedstock×CO conversion rate % (1-$CO_2$ selectivity N)]×100%;

Effective product selectivity %=[1−$CO_2$ Selectivity %−$CH_4$ Selectivity %]×100%.

Example 1

The example was used for illustrating a supported ɛ/ɛ' iron carbide catalyst and preparation method thereof (For the sake of facilitating comparison, all the raw materials were derived from the same company, but the raw materials were not limited to the company during the actual operation).

(1) The ferric nitrate nonahydrate crystal was taken and completely dissolved in purified water to prepare a ferric nitrate solution (with the concentration of 0.12 g/mL); another 10.0 g of silica carrier having a particle size of 30-200 μm (the silica carrier was purchased from the Sinopharm Chemical Reagent Co., Ltd.) was taken, the silica carrier was subjected to saturation dipping in the ferric nitrate solution such that the content of Fe in the dipped carrier was 30 wt %, and the dipped silica carrier was subjected to drying at 30° C. for 0.5 h;

(2) The dipped carrier was put into a vacuum oven for drying under the set vacuum degree of 250 Pa and the temperature of 35° C. for 10 hours, and was then subjected to drying in a baking oven at the temperature of 110° C. for 24 hours;

(3) The dried dipped carrier was put into a muffle furnace for roasting at 500° C. for 1 hour to obtain a precursor 1;

(4) The precursor 1 was placed in a tubular Fischer-Tropsch synthesis reactor, and the $H_2$ flow with the gas velocity of 2,800 mL/h/g, the pressure of 2.6 atmospheric pressure and the temperature of 550° C. was introduced to react for 1 hour;

(5) The temperature in the reactor was reduced to 185° C., and the $H_2$ flow was switched to the ($H_2$+CO) gas flow having a molar ratio of $H_2$/CO=1.2, a gas velocity of 9,000 mL/h/g and a total pressure of 0.08 atmospheric pressure, and the pretreatment reaction was carried out for 90 min;

(6) The gas flow in the reactor was switched to the ($H_2$+CO) gas flow having a molar ratio $H_2$/CO=3.2, a gas velocity of 25,000 mL/h/g and a total pressure of 0.2 atmospheric pressure, in the meanwhile, the temperature was steadily raised to 290° C. at a temperature rise rate of 2.5° C./min, the temperature was maintained for 2.5 h. The supported ɛ/ɛ' iron carbide catalyst was prepared, which was labeled as the ɛ/ɛ' iron carbide catalyst A1.

Figure 2:
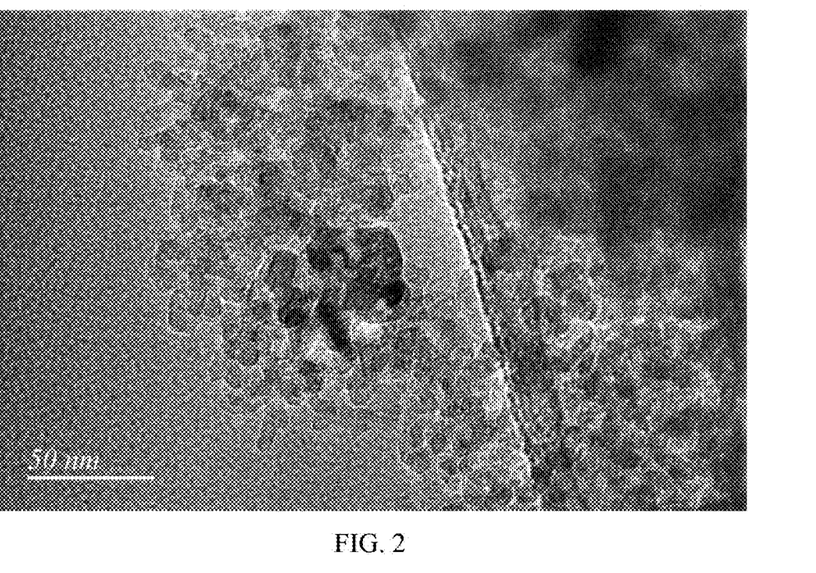
FIG. 2 illustrates a Transmission Electron Microscopy (TEM) image of the precursor 1 in Example 1.
Figure 3:
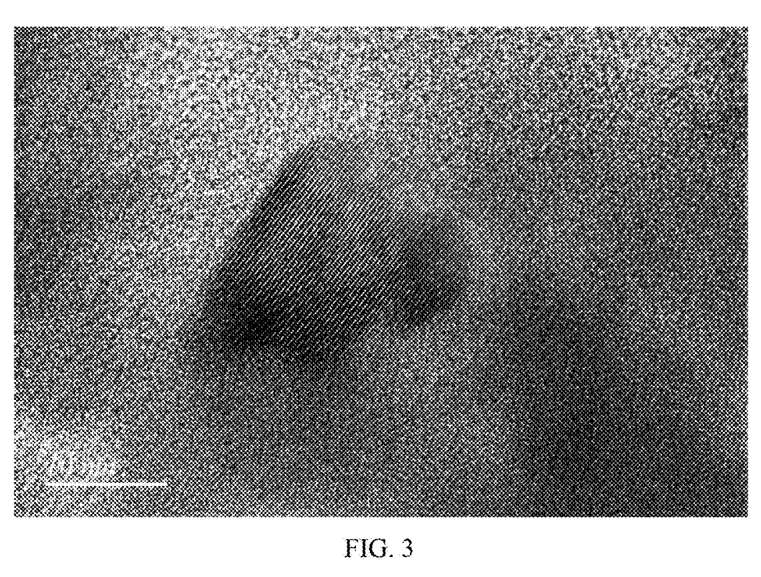
FIG. 3 illustrates a high resolution transmission electron microscope (HRTEM) image of the precursor 1 in Example 1.

Testing:

The precursor 1 was taken and subjected to Transmission Electron Microscopy (TEM) and High Resolution Transmission Electron Microscopy (HRTEM) measurements, and the measurement results were shown in FIG. 2 and FIG. 3 respectively.

Figure 4:
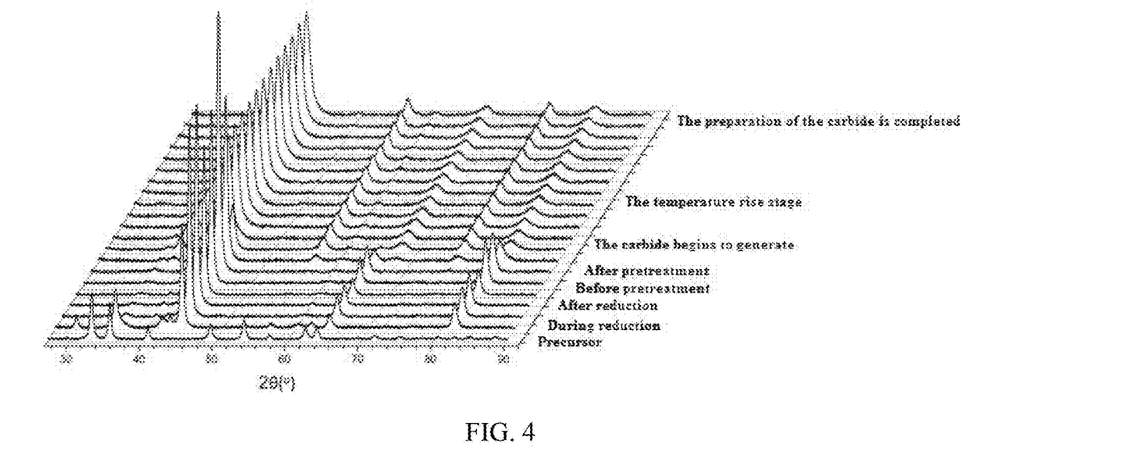
FIG. 4 shows an in situ X-ray Diffraction (XRD) pattern of the preparation of ε/ε' iron carbide catalyst A of Example 1.
Figure 5:
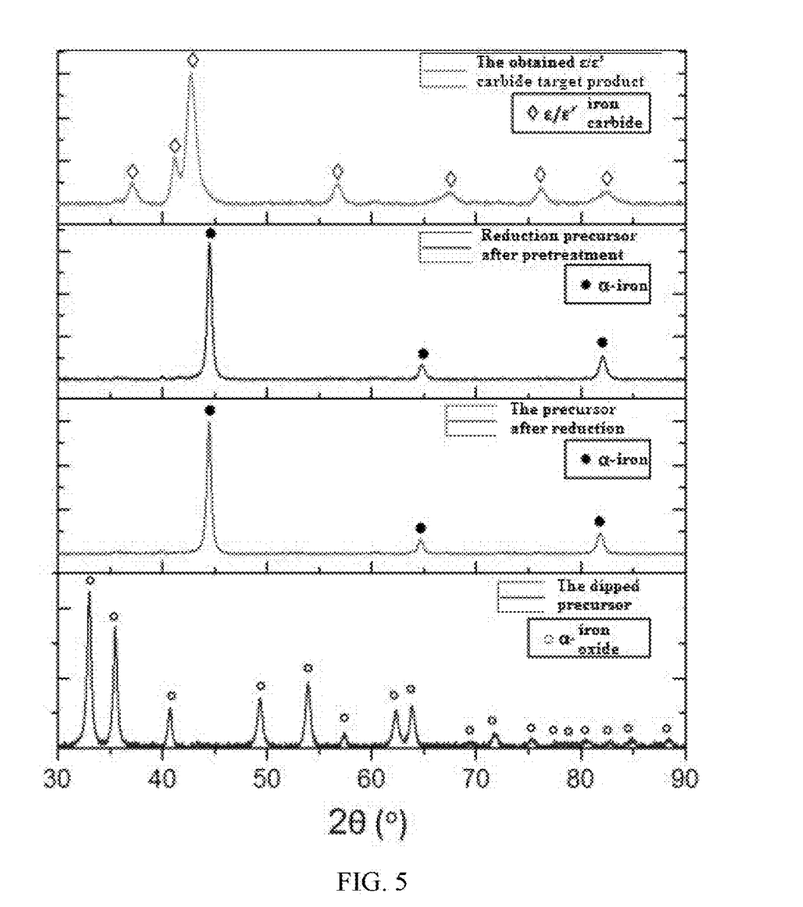
FIG. 5 illustrates an in situ XRD pattern of ε/ε' iron carbide catalyst A obtained in Example 1.

The in situ XRD detection technique was adopted, that is, the aforementioned catalyst preparation process was carried out while monitoring the change of crystalline phase of the materials using an X-ray Diffractometer (the XFD was commercially available from Rigaku Corporation, model D/max-2600/PC), the results were shown in FIG. 4 and FIG. 5.

Wherein the transition process from the precursor 1 ($\alpha$-$Fe_2O_3$ phase) to the target carbide (ɛ/ɛ' iron carbide phase) was clearly visible in FIG. 4; as can be seen from FIG. 5, the prepared target product ɛ/ɛ' iron carbide illustrated the desirable crystallinity, the product ɛ/ɛ' iron carbide perfectly corresponded to all characteristic peaks of the ɛ/ɛ' iron carbide, the purity was extremely high, and the product did not contain any other impurity.

An in-situ Mossbauer spectrum detection technology was adopted, namely a Mossbauer spectrum (Transmission $^{57}$Fe, $^{57}$Co (Rh) source sinusoidal velocity spectrometer) was used for monitoring the component change of the materials during the preparation process, a treatment method for adding 250° C. saturated vapor pressure water steam into reaction gas was performed on the target product active phase ɛ/ɛ' iron carbide, such that the condition after long-period operation under the industrial conditions was simulated. The change process from the precursor 1 to the target carbide and the situation after long-term operation under the simulated industrial conditions through high-temperature water vapor treatment were clearly visible through the in-situ Mossbauer spectrum monitoring. The results were illustrated in FIG. 6 and Table 1.

Figure 6:
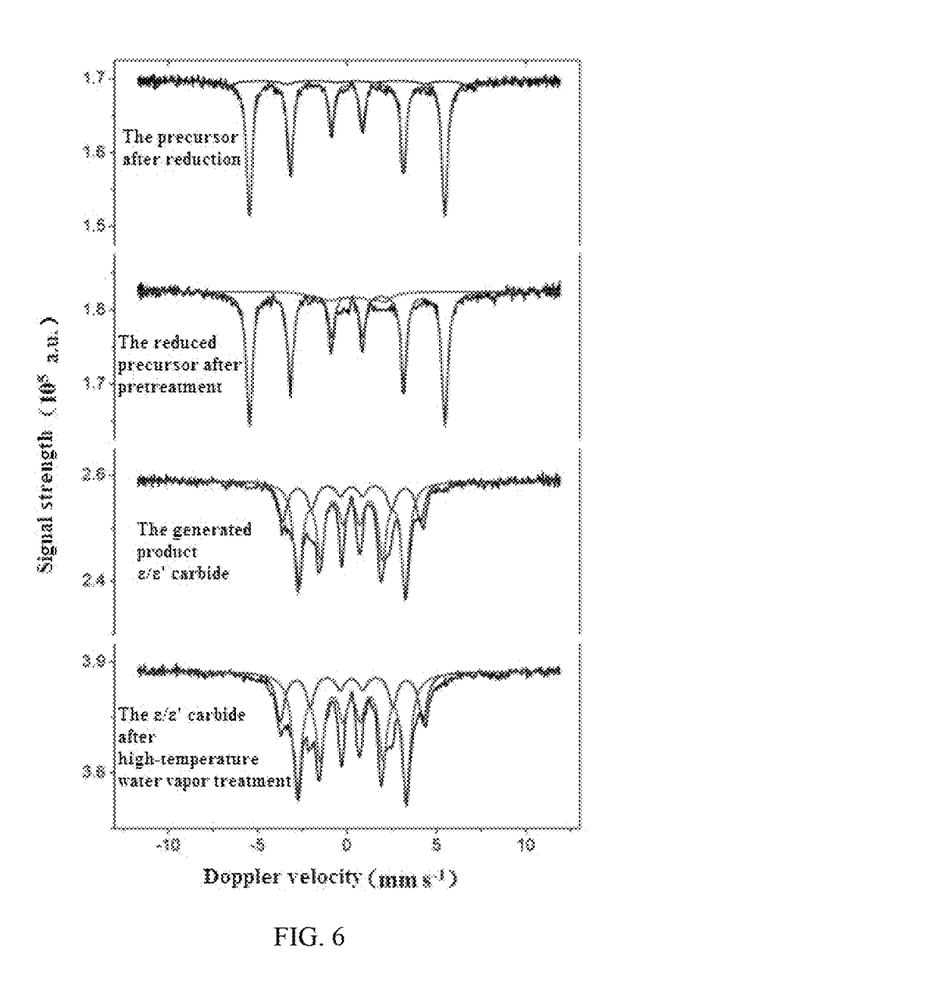
FIG. 6 illustrates an in situ Mossbauer spectrogram of the preparation process of ε/ε' iron carbide catalyst A in Example 1

FIG. 6 clearly illustrated the process of change from the precursor to the target carbide and the process of subjecting to the high-temperature water vapor treatment.

Table 1 showed the statistics of specific data of phase transformation, the purity of the active phase ɛ/ɛ' iron carbide in the target product prepared in Example 1 was 100%, and the purity was still 100% after long-term operation under simulated industrial conditions, as illustrated in Table L It demonstrated that the method of the present disclosure can be used for preparing a supported catalyst of active phase ɛ/ɛ' iron carbide with a purity of 100%, and the supported ɛ/ɛ' iron carbide catalyst obtained with the preparation method of the present disclosure can stably exist at a high temperature of 250° C., and furthermore, the active phase ɛ/ɛ' iron carbide in the catalyst can still maintain 100% purity even after the corrosion of the simulated industrial high temperature and high pressure water steam.

TABLE 1

| Treatment conditions | Phase | Molar content of the phase |
|---|---|---|
| The precursor after reduction | $Fe^0$ | 94% |
|  | $Fe^{3+}$ | 6% |
| The raw materials after pretreatment | $Fe^0$ | 88% |
|  | $Fe_xC$ | 12% |
| The active phase ɛ/ɛ' iron carbide in the generated product | ɛ'-$Fe_{2.2}$C/ ɛ -$Fe_2$C | 100% |
| The active phase ɛ/ɛ' iron carbide alter long-period operation under the simulated industrial conditions | ɛ'-$Fe_{2.2}$C/ ɛ -$Fe_2$C | 100% |

Example 2

(1) The ferrous ammonium sulfate crystal was taken and completely dissolved in purified water to prepare a ferrous ammonium sulfate solution (with the concentration of 0.08 g/mL); another 8.0 g, of alumina carrier having a particle size of 30-200 μm (purchased from the Sinopharm Chemical Reagent Co., Ltd.) was taken, the alumina carrier was subjected to saturation dipping in the ferrous ammonium sulfate solution such that the content of Fe in the dipped carrier was 10 wt %, and the dipped alumina carrier was subjected to drying at 20° C. for 4 h;

(2) The dipped carrier was put into a vacuum oven for drying under the set vacuum degree of 1,200 Pa and the temperature of 80° C. for 6 hours, and was then subjected to drying in a baking oven at the temperature of 110° C. for 3 hours;

(3) The dried dipped carrier was put into a muffle furnace for roasting at 300° C. for 10 hours to obtain a precursor 2;

(4) The precursor 2 was placed in a tubular Fischer-Tropsch synthesis reactor, and the $H_2$ flow with the gas velocity of 22,000 mL/h/g, the pressure of 0.3 atmospheric pressure and the temperature of 350° C. was introduced to react for 12 hour;

(5) The temperature in the reactor was reduced to 90° C., and the $H_2$ flow was switched to the ($H_2$+CO) gas flow having a molar ratio of $H_2$/CO=2.8, a gas velocity of 1,500 mL/h/g and a total pressure of 4.5 atmospheric pressure, and the pretreatment reaction was carried out for 20 min;

(6) The gas flow in the reactor was switched to the ($H_2$+CO) gas flow with a molar ratio $H_2$/CO=1.0, a gas velocity of 3,000 mL/h/g and a total pressure of 4.5 atmospheric pressure, in the meanwhile, the temperature was steadily raised to 210° C. at a temperature rise rate of 0.2° C./min, the temperature was maintained for 12 hours. The supported ε/ε' iron carbide catalyst was prepared, which was labeled as the ε/ε' iron carbide catalyst A2.

Example 3

(1) The ferric chloride crystal was taken and completely dissolved in purified water to prepare a ferric chloride solution (with the concentration of 0.1 g/mL); another 11.0 g of titania carrier having a particle size of 30-200 μm (purchased from the Sinopharm Chemical Reagent Co., Ltd.) was taken, the titania carrier was subjected to saturation dipping in the ferric chloride solution such that the content of Fe in the dipped carrier was 19 wt %, and the dipped carrier was subjected to drying at 25° C. for 2 h;

(2) the dipped carrier was put into a vacuum oven for drying under the set vacuum degree of 450 Pa and the temperature of 70° C. for 9 hours, and was then subjected to drying in a baking oven at the temperature of 130° C. for 5 hours;

(3) the dried dipped carrier was put into a muffle furnace for roasting at 500° C. for 6 hours to obtain a precursor 3;

(4) the precursor 3 was placed in a tubular Fischer-Tropsch synthesis reactor, and the $H_2$ flow with the gas velocity of 7,000 mL/h/g, the pressure of 1.6 atmospheric pressure and the temperature of 420° C. was introduced to react for 8 hours;

(5) the temperature in the reactor was reduced to 127° C., and the $H_2$ flow was switched to the ($H_2$+CO) gas flow having a molar ratio of $H_2$/CO=2.3, a gas velocity of 5,000 and a total pressure of 0.5 atmospheric pressure, and the pretreatment reaction was carried out for 80 min;

(6) the gas flow in the reactor was switched to the ($H_2$+CO) gas flow with a molar ratio $H_2$/CO=2.7, a gas velocity of 5,000 mL/h/g and a total pressure of 2.5 atmospheric pressure, in the meanwhile, the temperature was steadily raised to 280° C. at a temperature rise rate of 1° C./min, the temperature was maintained for 8 h. The supported ε/ε' iron carbide catalyst was prepared, which was labeled as the ε/ε' iron carbide catalyst A3.

Example 4

A supported de' iron carbide catalyst was prepared according to the method of Example 1, except that in step (4), the pressure of the $H_2$ flow was 15 atmospheres. The ε/ε' iron carbide catalyst A4 was prepared.

Example 5

A supported ε/ε' iron carbide catalyst was prepared according to the method of Example 1, except that in step (4), the gas velocity of $H_2$ flow was 600 mL/h/g. The ε/ε' iron carbide catalyst A5 was prepared.

Example 6

A supported ε/ε' iron carbide catalyst was prepared according to the method of Example 1, except that in step (5), the pressure of the ($H_2$+CO) gas flow was 7 atmospheric pressure. The ε/ε' iron carbide catalyst A6 was prepared.

Example 7

A supported ε/ε' iron carbide catalyst was prepared according to the method of Example 1, except that in step (5), the gas velocity of the ($H_2$+CO) gas flow was 300 ML/h/g. The ε/ε' iron carbide catalyst A7 was prepared.

Example 8

A supported ε/ε' iron carbide catalyst was prepared according to the method of Example 1, except that in step (6), the pressure of the ($H_2$+CO) gas flow was 0.1 atmospheric pressure. The ε/ε' iron carbide catalyst A8 was prepared.

Example 9

A supported ε/ε' iron carbide catalyst was prepared according to the method of Example 1, except that in step (6), the gas velocity of the ($H_2$+CO) gas flow was 30,000 mL/h/g. The ε/ε' iron carbide catalyst A9 was prepared.

Example 10

A supported ε/ε' iron carbide catalyst was prepared according to the method of Example 1, except that in step (6), the temperature rise rate was 5° C./min. The ε/ε' iron carbide catalyst A1.0 was prepared.

Comparative Example 1

A supported ε/ε' iron carbide catalyst was prepared according to the method of Example 1, except that the material obtained in the step (4) was directly treated according to the step (6) without performing the step (5). The iron carbide catalyst D1 was prepared.

Comparative Example 2

A supported ε/ε' iron carbide catalyst was prepared according to the method of Example 1, except that in step (5), the molar ratio of $H_2$/CO was 1.0. The iron carbide catalyst D2 was prepared.

Comparative Example 3

A supported ε/ε' iron carbide catalyst was prepared according to the method of Example 1, except that in step (6), the molar ratio of $H_2$/CO was 3.5. The iron carbide catalyst D3 was prepared.

Comparative Example 4

A supported ε/ε' iron carbide catalyst was prepared according to the method of Example 1, except that the pretreatment temperature M step (5) was 200° C., and the temperature of carbide preparation in step (6) was 310° C. The iron carbide catalyst D4 was prepared.

Comparative Example 5

The comparative example served to illustrate a method for preparing iron carbide catalysts in the prior art (N. Lohitham et al./*Journal of Catalysis* 255 (2008) 104-113).

(1) According to the molar ratio of 100Fe/5Cu/17Si, 0.6 mol/L of Fe(NO$_3$)$_3$·9H$_2$O and CuN$_2$O$_6$·3H$_2$O in the raw materials were mixed, 60 ml of H$_2$O was added for dissolution, another ingredient Si(OC$_2$H$_5$)$_4$ was taken and added into 40 mL of propanol for dissolution. The two solutions obtained above were mixed, and heated to a temperature of 83±3° C.;

(2) 2.7 mol/L NH$_4$OH solution was preheated to 83±3° C.;

(3) The NH$_4$OH solution obtained in the step (2) was continuously added into the mixed solution obtained in the step (1), and the blended solution was stirred vigorously until a precipitate was generated, wherein the pH=8-9 was maintained at the end point of the precipitation. The precipitation was subjected to aging at room temperature for 17 hours, and washed thoroughly with 1.3-1.5 L deionized water to remove NH$_3$ till pH=7-8. The washed precipitate was subjected to drying at 110° C. for 18-24 hours, and calcinating at 300° C. in air for 5 hours, and was cooled to room temperature within 2 hours;

(4) The material with a particle size less than 90 μm was sieved, and subjected to activation under the typical industrial catalyst activation conditions consisting of a H$_2$/CO molar ratio of 1.0, a total gas velocity of 5,000 mL/h/g, and a temperature of 260° C. for 12 h, the iron carbide catalyst D5 was prepared.

Test Example (1) The Mossbauer spectroscopy was used to measure the molar content of the ε'-Fe$_{2.2}$C/ε-Fe$_2$C phases in the active phases of the product catalysts A2-A10 and D1-D5, respectively. The results were shown in Table 2.

(2) Under the conditions consisting of a molar ratio of reaction gases H$_2$/CO=1.5, a pressure 2.4 MPa, a temperature 235° C. and a total gas velocity (H$_2$+CO) of 20,000 mL/h/g, the product catalysts A1-A10 and D1-D5 were respectively contacted with the reaction gases H$_2$ and CO to carry out the Fischer-Tropsch synthesis reaction. The catalyst activity and product selectivity of the catalysts were monitored at 10 h and 400 h of reaction. The results were shown in Table 3.

TABLE 2

|  | A1 | A2 | A3 | A4 | A5 | A6 | A.7 | A8 |
|---|---|---|---|---|---|---|---|---|
| ε'-Fe$_{2.2}$C/ ε -Fe$_2$C molar content | 100% | 100% | 100% | 100% | 100% | 100% | 100% | 100% |

|  | A9 | A10 | D1 | D2 | D3 | D4 | D5 |
|---|---|---|---|---|---|---|---|
| ε'-Fe$_{2.2}$C/ ε - Fe$_2$C molar content | 100% | 100% | 61% | 50% | 68% | 55% | 18% |

The results of Table 2 illustrate that the catalyst having 100% pure phase of ε/ε' iron carbide can be prepared with the preparation method of the present disclosure.

TABLE 3

| Reaction time h | CO conversion rate mmol/h/g-Fe | | CO$_2$ selectivity %* | | CH$_4$ selectivity % | | Effective product selectivity %# | |
|---|---|---|---|---|---|---|---|---|
|  | 10 | 400 | 10 | 400 | 10 | 400 | 10 | 400 |
| A1 | 180.7 | 180.7 | 0.5 | 0.5 | 8.7 | 8.9 | 90.8 | 90.6 |
| A2 | 160.8 | 160.2 | 1.4 | 1.5 | 8.7 | 8.8 | 89.9 | 89.7 |
| A3 | 149.5 | 148.7 | 1.9 | 2.0 | 9.1 | 9.4 | 89 | 88.6 |
| A4 | 125.6 | 122.3 | 2.6 | 3 | 11.5 | 12.5 | 85.9 | 84.5 |
| A5 | 110.8 | 106.3 | 3 | 3.5 | 12.3 | 13.3 | 84.7 | 83.2 |
| A6 | 130.6 | 126.1 | 2.6 | 2.9 | 11.8 | 12.6 | 85.6 | 84.5 |
| A7 | 140.6 | 136.6 | 3.2 | 3.6 | 13.2 | 13.2 | 83.6 | 83.2 |
| A8 | 120.8 | 116.3 | 4 | 4.6 | 12.6 | 12.9 | 83.4 | 82.5 |
| A9 | 118.8 | 116.6 | 2.3 | 2.8 | 10.9 | 10.3 | 86.8 | 86.9 |
| A10 | 139.9 | 135.9 | 3.5 | 3.5 | 10.2 | 10.5 | 86.3 | 86 |
| D1 | 80.3 | 72.1 | 18.3 | 20.9 | 15.3 | 18.3 | 66.4 | 60.8 |
| D2 | 73.8 | 68.6 | 16.7 | 19.3 | 16.2 | 19 | 67.1 | 61.7 |
| D3 | 85.6 | 79.3 | 22.3 | 25.4 | 15.3 | 18.7 | 62.4 | 55.9 |
| D4 | 90.2 | 80.6 | 20.3 | 23.6 | 17 | 20.3 | 62.7 | 56.1 |
| D5 | 31.3 | 27.6 | 28.5 | 33.7 | 18.6 | 23.5 | 52.9 | 42.8 |

Note*:
each of the aforementioned selectivities is based on the total CO conversion amount;

Notes#:
the effective product selectivity refers to the selectivity of products other than the by-products CO$_2$ and CH$_4$.

As can be seen from the results in Table 3, the supported ε/ε' iron carbide catalyst prepared with the method of the present disclosure exhibits ultra-low CO$_2$ selectivity under the industrial conditions, preferably, the CO$_2$ selectivity may be lower than 2.5%, even close to zero; in contrast, the CO$_2$ selectivity of the iron carbide catalyst D5 prepared by the prior art under the same industrial conditions is as high as 28.5%-33.7%.

Moreover, the CH$_4$ selectivity of the active phase ε/ε' iron carbide catalyst prepared with the method of the present disclosure is lower than 13.5% (preferably lower than 9.5%), and the selectivity of effective products can reach 82% or more (preferably higher than 88%); while the iron carbide catalyst D5 prepared by the prior art has high CH$_4$ selectivity, low effective product selectivity and low CO utilization efficiency.

Finally, the experimental data at an elapse of the 10 hour and the 400 hour are compared, the results reveals that the supported ε/ε' iron carbide catalyst prepared with the method disclosed by the present disclosure keeps stable and shows no obvious change in both the CO conversion rate and the product selectivity after reacting for 400 hours; however, various parameters of the iron carbide catalyst D5 prepared by the prior art are obviously degraded, it demonstrates that the stability of the supported ε/ε' iron carbide catalyst prepared with the method of the present disclosure is significantly superior to that of the iron carbide catalyst in the prior art.

The above content describes in detail the preferred embodiments of the present disclosure, but the present disclosure is not limited thereto. A variety of simple modifications can be made in regard to the technical solutions of the present disclosure within the scope of the technical concept of the present disclosure, including a combination of individual technical features in any other suitable manner, such simple modifications and combinations thereof shall also be regarded as the content disclosed by the present disclosure, each of them fills into the protection scope of the present disclosure.

The invention claimed is:
1. A method of preparing a supported ε/ε' iron carbide catalyst for Fischer-Tropsch synthesis reaction, wherein the preparation method comprises the following steps:

(1) dipping a catalyst carrier in a ferric salt aqueous solution, drying and roasting the dipped carrier to obtain a catalyst precursor;
(2) subjecting the catalyst precursor and $H_2$ to a precursor reduction at the temperature of 300-550° C.;
(3) pretreating the material obtained in the step (2) with $H_2$ and CO at the temperature of 90-185° C., wherein the molar ratio of $H_2$/CO is 1.2-2.8: 1;
(4) preparing carbide with the material obtained in the step (3), $H_2$ and CO at the temperature of 200-300° C., wherein the molar ratio of $H_2$/CO is 1.0-3.2: 1.

2. The method of claim 1, wherein the ferric salt is at least one selected from the group consisting of iron nitrate, iron chloride and ferrous ammonium sulfate.

3. The method of claim 1, wherein the dipping is performed such that the iron content in the dipped carrier after drying is within a range of 10-30 wt %.

4. The method of claim 1, wherein the drying and roasting process comprises: firstly drying the dipped carrier at 20-30° C. for 0.5-4h, then stoving the dipped carrier at 35-80° C. and the vacuum degree of 250-1,200 Pa for 6-10h, drying the stoved material at 110-150° C. for 3-24h, and then roasting the obtained material at 300-550° C. for 1-10h.

5. The method of claim 1, wherein the catalyst carrier is at least one selected from the group consisting of silica, alumina and titania.

6. The method of claim 1, wherein the catalyst carrier has a particle size within a range of 30-200 μm.

7. The method of claim 1, wherein in the step (2), the pressure of the precursor reduction is within a range of 0.1-15 atmospheric pressure; the time is within a range of 0.7-15h; the gas velocity of $H_2$ in the step (2) is within a range of 600-25,000 mL/h/g.

8. The method of claim 7, wherein in the step (2), the pressure of the precursor reduction is within a range of 0.3-2.6 atmospheric pressure; the time is within a range of 1-12h; the gas velocity of $H_2$ in the step (2) is within a range of 2,800-22,000 mL/h/g.

9. The method of claim 1, wherein in the step (3), the pressure of the pretreatment process is within a range of 0.05-7 atmospheric pressure; the time is within a range of 15-120 min; the total gas velocity of $H_2$ and CO in the step (3) is within a range of 300-12,000 mL/h/g.

10. The method of claim 9, wherein in the step (3), the pressure of the pretreatment process is within a range of 0.08-4.5 atmospheric pressure; the time is within a range of 20-90 min; the total gas velocity of $H_2$ and CO in the step (3) is within a range of 1,500-9,000 mL/h/g.

11. The method of claim 1, wherein in the step (4), the pressure of the carbide preparation in step (4) is within a range of 0.1-10 atmospheric pressure; the time is within a range of 1.5-15h; the total gas velocity of $H_2$ and CO in the step (4) is within a range of 500-30,000 mL/h/g.

12. The method of claim 11, wherein in the step (4), the pressure of the carbide preparation in step (4) is within a range of 0.2-4.5 atmospheric pressure; the time is within a range of 2.5-12h; the total gas velocity of $H_2$ and CO in the step (4) is within a range of 3,000-25,000 mL/h/g.

13. The method of claim 1, wherein the method further comprises: the system temperature after the pretreatment is increased to 200-300° C. at the heating rate of 0.2-5° C./min.

14. The method of claim 13, wherein the system temperature after the pretreatment is increased to 210-290° C. at a heating rate of 0.2-2.5° C./min.

15. The method of claim 1, wherein the precursor reduction, pretreatment and carbide preparation process is carried out in a Fischer-Tropsch synthesis reactor.

16. A supported ε/ε' iron carbide catalyst for Fischer-Tropsch synthesis reaction obtained with the method of claim 1.

17. A Fischer-Tropsch synthesis process comprising: contacting a synthesis feed gas with a catalyst under the Fischer-Tropsch synthesis reaction conditions, wherein the catalyst is the supported ε/ε' iron carbide catalyst for the Fischer-Tropsch synthesis reaction of claim 9.

18. The process of claim 17, wherein the Fischer-Tropsch synthesis is carried out in a high temperature and high pressure continuous reactor.

* * * * *